(12) United States Patent
Zhou et al.

(10) Patent No.: US 8,044,212 B2
(45) Date of Patent: Oct. 25, 2011

(54) RECONFIGURABLE MOLECULES AND MOLECULAR SWITCHES, SENSORS, AND DYES EMPLOYING THE SAME

(75) Inventors: Zhang-Lin Zhou, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 620 days.

(21) Appl. No.: 11/799,147

(22) Filed: Apr. 30, 2007

(65) Prior Publication Data

US 2008/0269486 A1    Oct. 30, 2008

(51) Int. Cl.
*C07D 235/02* (2006.01)

(52) U.S. Cl. .......... 548/110; 250/338.1; 250/338.4; 252/500; 257/40; 257/741

(58) Field of Classification Search .......... 548/110
See application file for complete search history.

(56) References Cited

U.S. PATENT DOCUMENTS

| | | | | |
|---|---|---|---|---|
| 5,274,113 | A * | 12/1993 | Kang et al. | 548/405 |
| 6,946,644 | B2 * | 9/2005 | Wood | 250/226 |
| 6,995,312 | B2 * | 2/2006 | Zhou et al. | 136/263 |

* cited by examiner

*Primary Examiner* — Laura L. Stockton

(57) ABSTRACT

Various embodiment of the present invention are directed to organic molecules that are reconfigurable under application of an external electric field. One organic molecule embodiment of the present invention has the structure:

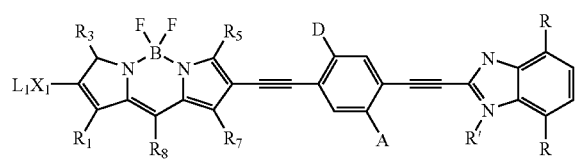

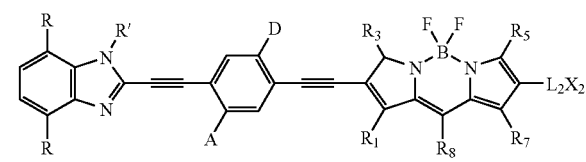

where $L_1X_1$ and $L_2X_2$ are optional connector groups, A represents an electron acceptor group, D represents an electron donor group, R and R' represent spacer molecules, and $R_1$, $R_2$, $R_3$, $R_4$, $R_5$, $R_6$, $R_7$, and $R_8$ represent atoms and hydrocarbons.

7 Claims, 11 Drawing Sheets

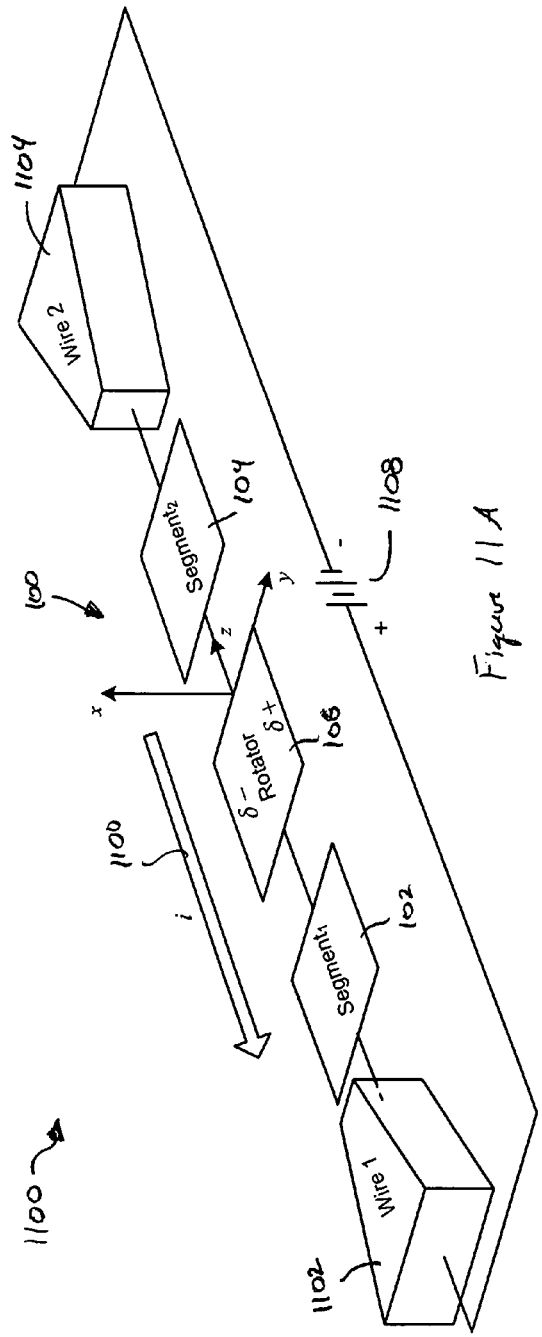
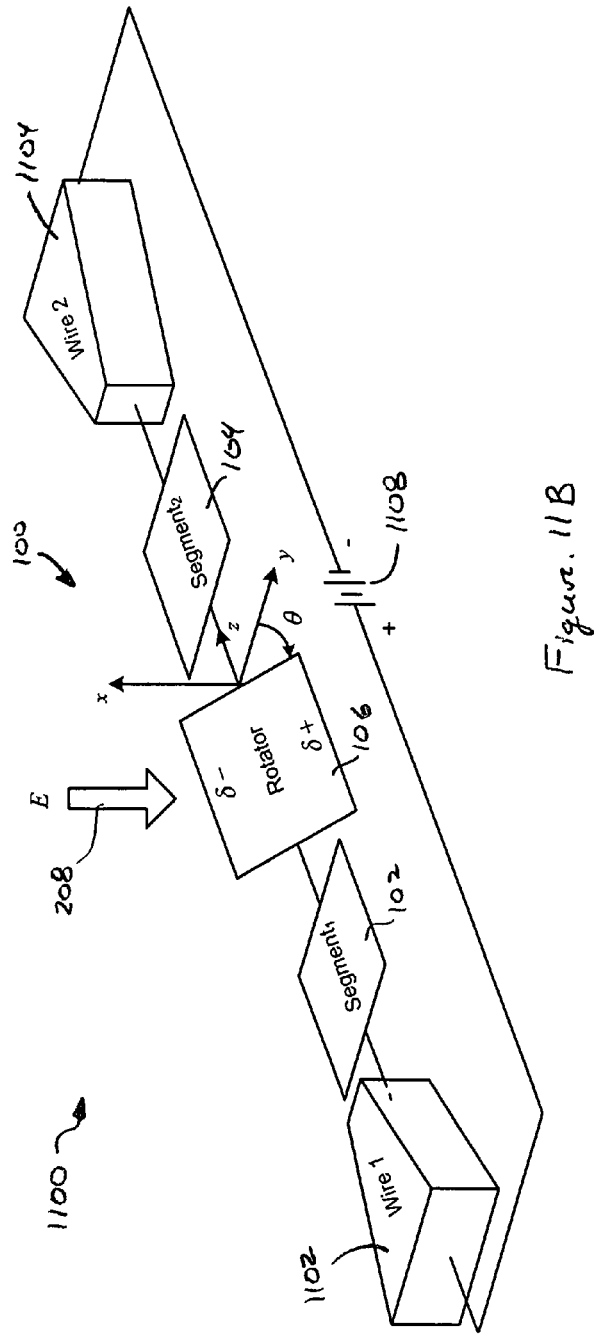
Figure 11A
Figure 11B

RECONFIGURABLE MOLECULES AND MOLECULAR SWITCHES, SENSORS, AND DYES EMPLOYING THE SAME

TECHNICAL FIELD

Embodiments of the present invention are directed to reconfigurable molecules, and, in particular, to reconfigurable molecules that can be employed as dyes, sensors, and molecular switches in microelectronic devices.

BACKGROUND

For the past four decades, inorganic materials and metals have been the backbone of the electronics industry. Semiconductor manufacturers have developed fabrication techniques that have enabled them to fabricate electronic components in inorganic materials and metals with microscale and nanoscale dimensions. For example, recent advances in lithographic and etching techniques have enabled semiconductor manufacturers to fabricate metal wires with nanoscale cross-sectional dimensions and semiconductor logic gates with widths less than a micron. However, within the next few decades, semiconductor manufactures are expected to reach limits to further manufacturing improvements in lithographic and etching techniques.

Advances and developments in materials science and chemistry may provide alternatives to using certain microscale and nanoscale inorganic and metal-based electronic components in microscale electronic devices. In recent years, chemists and materials scientists have begun to develop organic molecules, including conjugated organic molecules, short-chain oligomers, and longer-chain polymers, that emit light, conduct current, and act as semiconductors. The ability of these organic molecules to transport charge and emit light is, in part, due to weak π-bond overlap of neighboring atoms. Chemists and materials scientists have recognized a need for organic molecules that have a broad range of microscale and nanoscale electronics applications. In particular, chemists and materials scientists have recognized a need for organic molecules that can be used in microscale and nanoscale devices, including memory, logic gates, electrical interconnections, electronic switching, illumination displays, and chemical detection devices.

SUMMARY

Various embodiment of the present invention are directed to organic molecules that are reconfigurable under application of an external electric field. One organic molecule embodiment of the present invention has the structure:

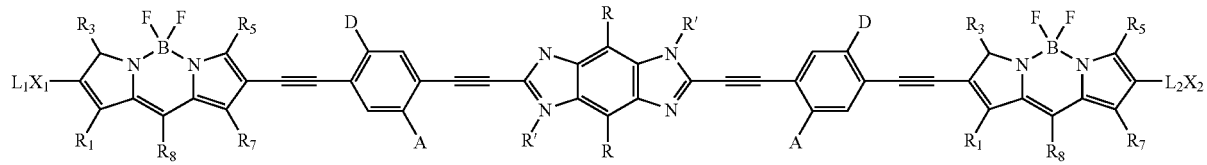

where $L_1X_1$ and $L_2X_2$ are optional connector groups, A represents an electron acceptor group, D represents an electron donor group, R and R' represent spacer molecules, and $R_1$, $R_2$, $R_3$, $R_4$, $R_5$, $R_6$, $R_7$, and $R_8$ represent atoms and hydrocarbons.

DESCRIPTIONS OF THE DRAWINGS

FIGS. 11A-11B illustrate use of the molecule shown in FIG. 1 as a molecular switch according to one embodiment of the present invention.

DESCRIPTION

Various embodiments of the present invention are directed to organic molecules that are reconfigurable under application of an external electric field. Various embodiments of the present invention can be used as dyes, sensors, and molecular switches and are used in sensing and molecular switching representing additional embodiments of the present invention.

Figure 1:
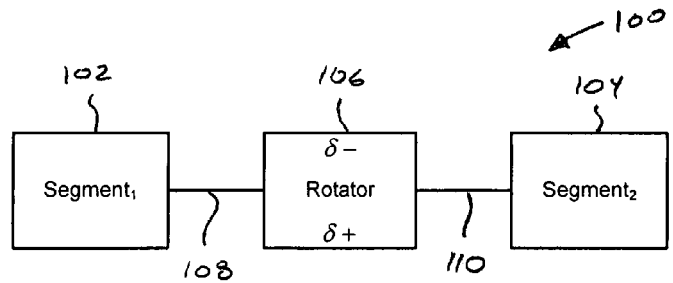
FIG. 1 shows a block diagram of an organic molecule that represents an embodiment of the present invention.

FIG. 1 shows a block diagram of an organic molecule that represents an embodiment of the present invention. An organic molecule 100 is composed of three physically distinct molecular segments. In particular, molecule 100 includes a first segment 102 and a second segment 104 connected to opposite ends of a third segment, called a "rotator" 106, via single covalent bonds 108 and 110, respectively. Rotator 106 represents a molecular moiety that can rotate under the influence of an externally applied electric field. For example, rotator 106 may be a molecule with a dipole moment directed approximately perpendicular to covalent bonds 108 and 110. As shown in FIG. 1, and in subsequent figures, the negatively charged pole is denoted by δ−, and the positively charged pole is denoted by δ+. Segments 102 and 104 are nonpolar molecular units.

Figure 2A:
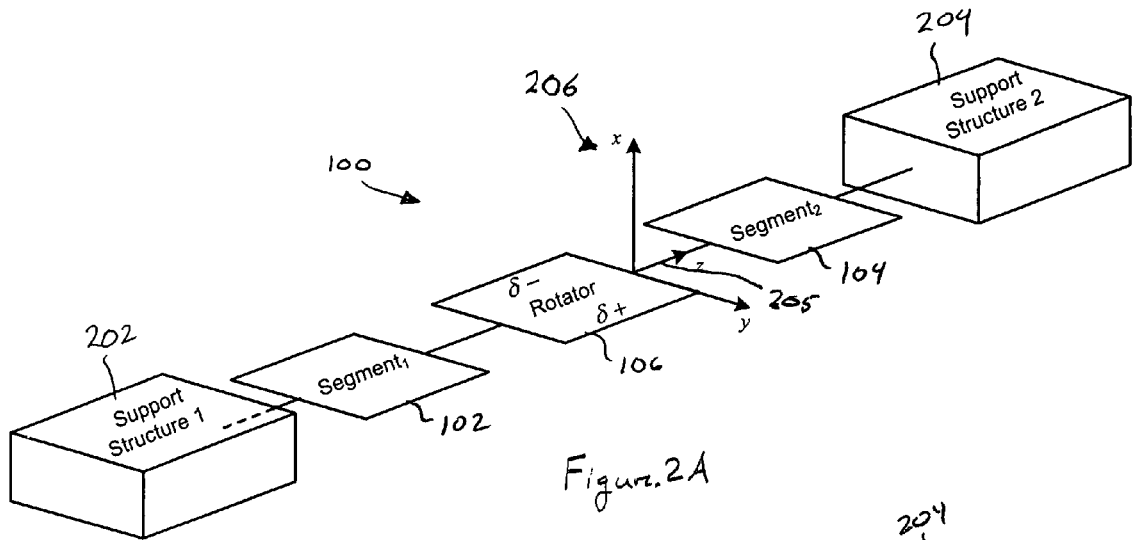
FIGS. 2A-2B shows how a rotator segment of the molecule shown in FIG. 1 can be rotated by applying an external electric field, according to one embodiment of the present invention.
Figure 2B:
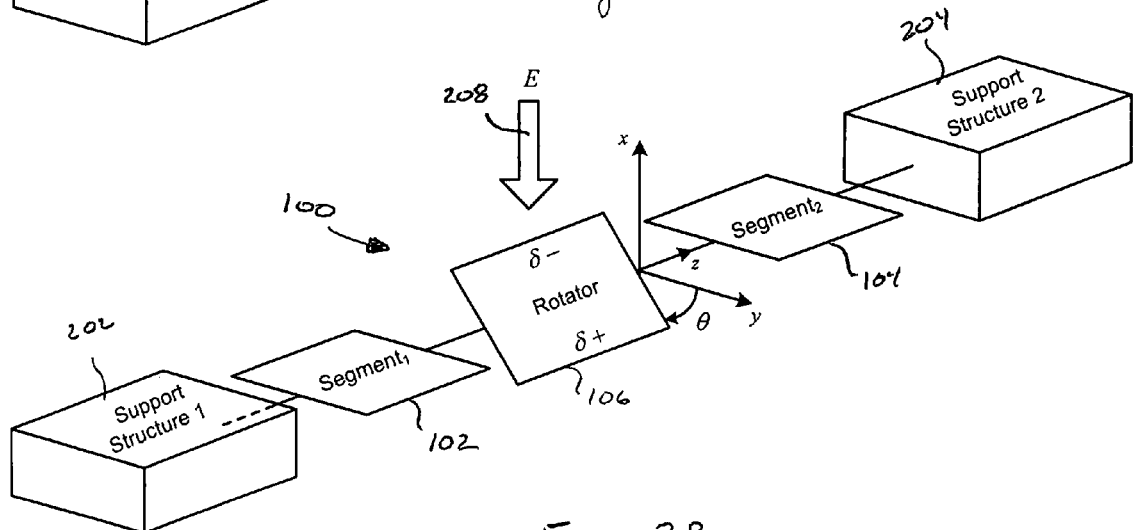

Segments 102, 104, and 106 can be composed of planar molecular systems exhibiting an approximately co-planar conformation when not perturbed by external stimuli. For example, segments 102, 104, and 106 can be composed of aromatic rings, planar fused rings, and planar heterocyclic molecules that are described in greater detail below, with reference to FIGS. 5-7. However, when an external stimulus with an appropriate magnitude and orientation is applied to molecule 100, such as an external electric field, rotator 106 rotates away from the approximately co-planar conformation. FIGS. 2A-2B shows how a rotator segment of the molecule shown in FIG. 1 can be rotated by applying an external electric field, according to one embodiment of the present invention. In FIGS. 2A-2B, molecule 100 is positioned between two support structures 202 and 204, with the central axis of the molecule 100 located along the z-coordinate axis 205 of a Cartesian coordinate system 206. Segment 102 is bonded to the support structure 202, and segment 104 is bonded to support structure 204. The bonds that link segments 102 and 104 to support structures 202 and 204 can be covalent, ionic, or hydrogen bonds. As shown in FIG. 2A, segments 102, 104, and 106 are initially co-planar and lie within the yz-plane. However, when an external electric field 208 is applied parallel to the x-coordinate axis, as shown in FIG. 2B, rotator 106 rotates away from the yz-plane by a rotation angle θ. The magnitude of the external electric field determines the amount of rotation. Although segments 102 and 104 are nonpolar molecules, an external electric field may induce a dipole moment in the segments 102 and 104, causing segments 102 and 104 to rotate. The strength of the external field and composition of segments 102 and 104 can be selected to reduce inducement of a dipole moment in segments 102 and 104.

Figure 3A:
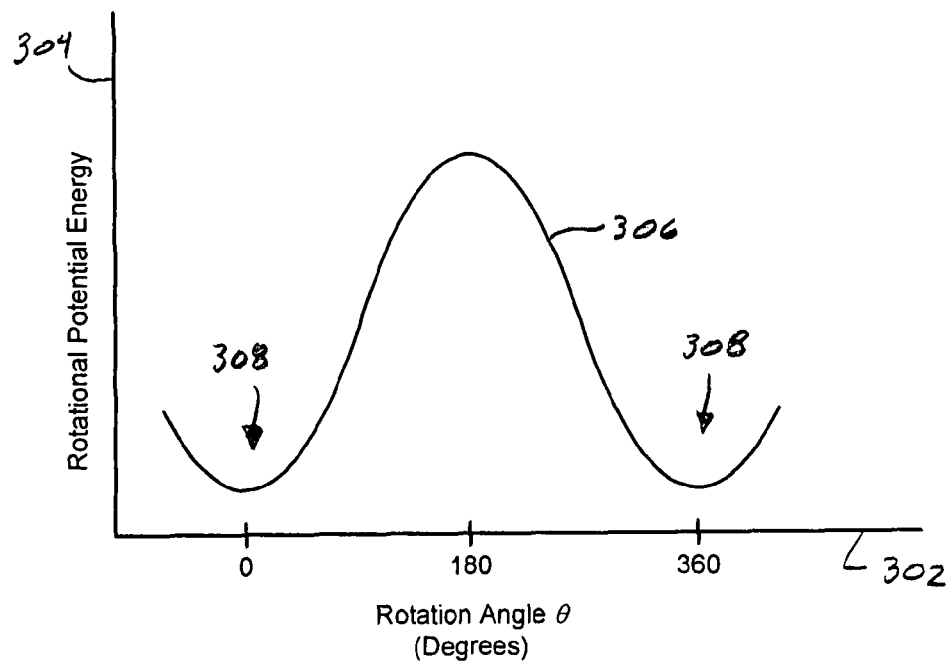
FIGS. 3A-3B are rotational-potential-energy plots associated with two hypothetical molecules that represent embodiments of the present invention.
Figure 3B:
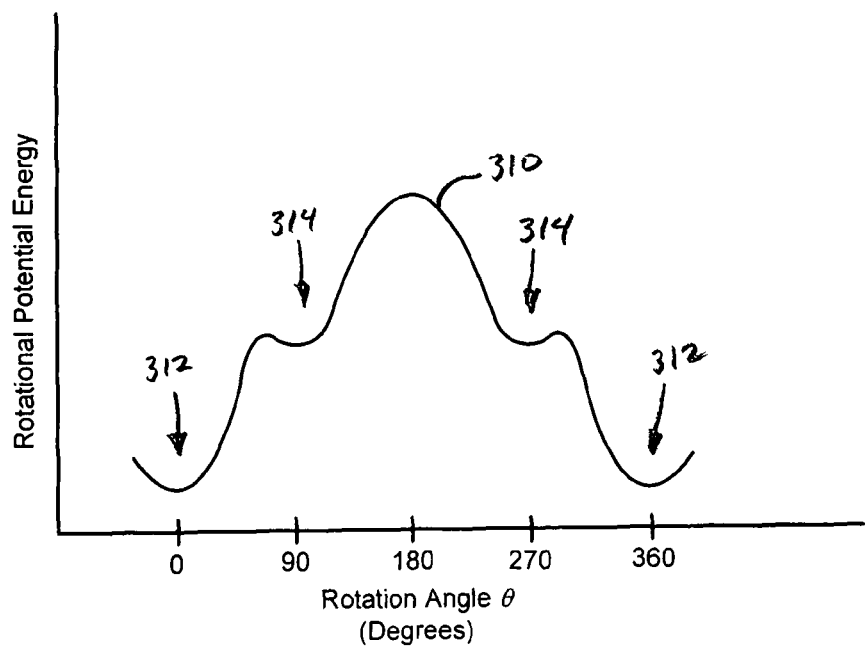

As the rotator 106 rotates away from the co-planar conformation, a large number of stable and unstable conformations may be possible. However, depending on the composition of segments 102, 104, and 106, not all of these conformations are energetically favored. FIGS. 3A-3B are rotational-potential-energy plots associated with two hypothetical molecules that represent embodiments of the present invention. Horizontal axes, such as horizontal axis 302, represent a range of rotation angles θ, and vertical axes, such as vertical axis 304, represent rotational-potential energy. Curve 306 shows how the rotational-potential energy changes as a rotator of a first hypothetical molecule is rotated through 360 degrees. A trough 308 corresponds to the planar conformation, which is the lowest energy, stable conformation. In particular, the curve 306 shows that the first molecule does not have a second stable rotation angle, and that in order to maintain a rotation angle other than 0 degrees, the external electric field must be maintained. In other words, when the external electric field is turned off, the rotator rotates back to the stable co-planar conformation. On the other hand, the curve 310 corresponds to a second hypothetical molecule that exhibits a lowest energy conformation corresponding to the co-planar conformation, as indicated by trough 312, and a second higher energy, less stable conformation with a rotation angle of 90 degrees, as indicated by trough 314. Other molecules in accordance with embodiments of the present invention may have three or more stable conformations and the associated rotational-potential energy curves may not be symmetric.

Many molecules that represent embodiments of the present invention are conjugated organic molecules. A conjugated organic molecule includes double bonds that are separated by just a single covalent bond. Organic molecules containing such conjugated double bonds tend to be more stable than similar organic molecules containing isolated double bonds separated by two or more single covalent bonds. Changing the rotational conformation about the single bonds between double bonds, in turn, changes the relative orientation of the conjugated double bonds. This, in turn, changes the electronic and light emitting properties of the molecule. In particular, when the rotator 106 of the molecule 100 is rotated away from the co-planar conformation, as described above with reference to FIG. 2, the conductivity and light-emitting properties of the molecule 100 are changed.

Figure 4A:
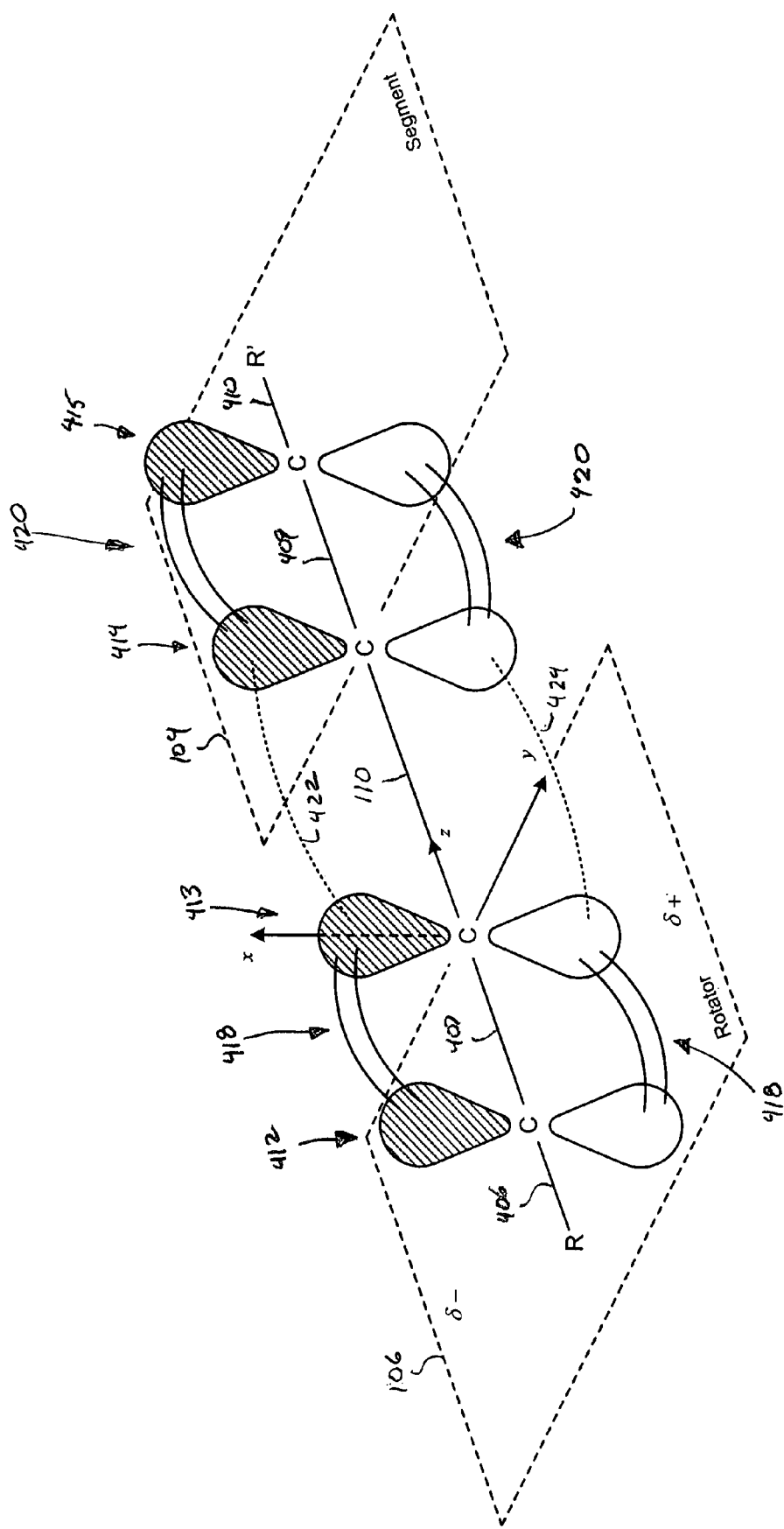
FIGS. 4A-4B show how a pair of conjugated double bonds are influenced by an external electric field.
Figure 4B:
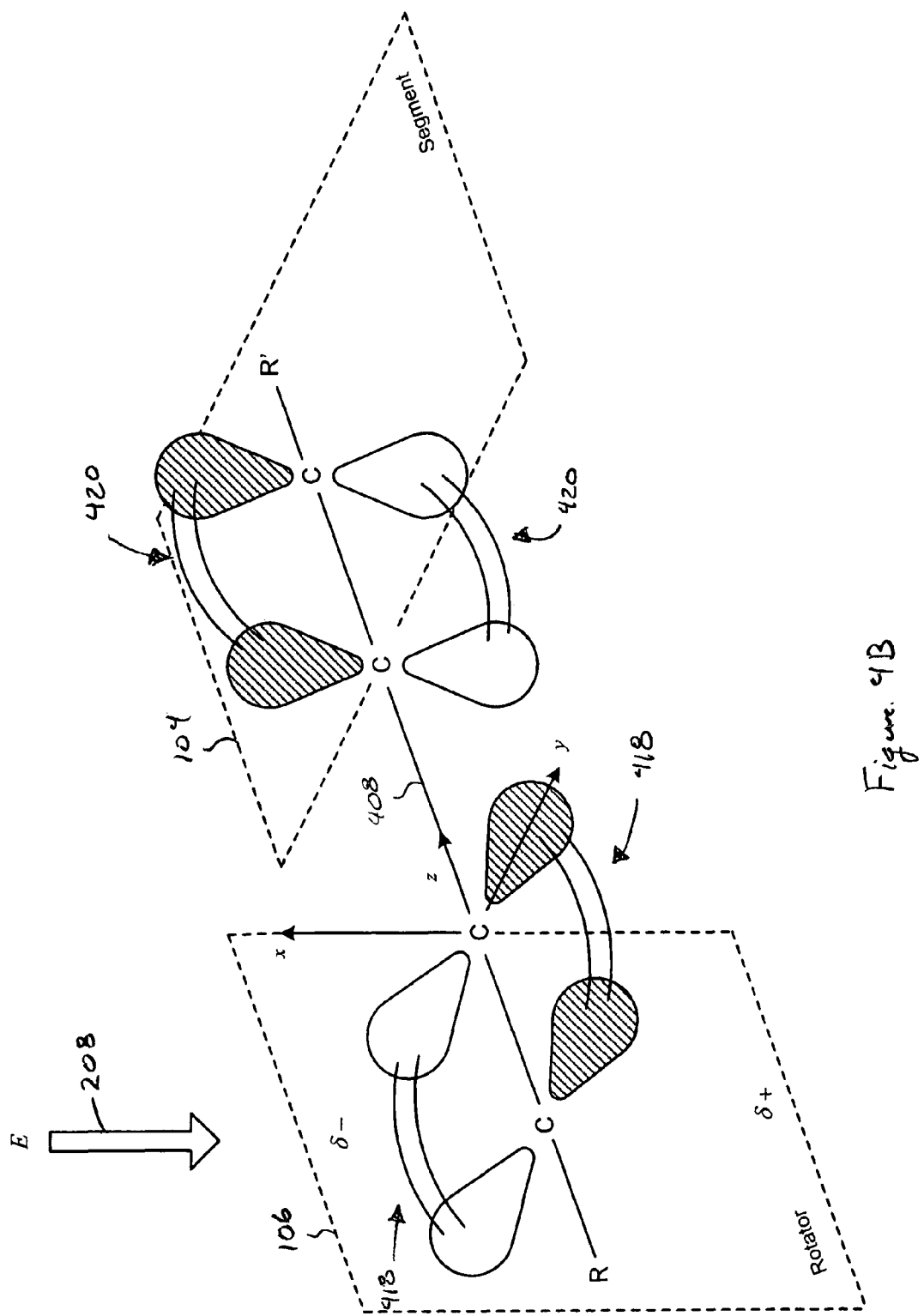

FIGS. 4A-4B show how a pair of conjugated double bonds are influenced by an external electric field. A double bond is viewed from the perspective of molecular orbital theory as a hybrid bond including a σ-bond and a π-bond, which are chemical bonds that that are responsible for holding atoms together to form molecules. A first double bond is located in rotator 106 of molecule 100. A second double bond is located in segment 104 of the same molecule 100. Line segments 406, 407, 409, and 410 represent single covalent, or σ, bonds that lie within the plane of rotator 106 and segment 104, and R and R' represent the remaining portions of rotator 106 and segment 104, respectively. As shown in FIG. 4A, four p-atomic orbitals ("AOs") 412-415 associated with the four C atoms are each represented by two lobes directed perpendicular to the plane of segments 104 and 106. A first π-bond 418 results from sideways overlap of the p AO's 412 and 413 and is indicated by curves connecting the lobes of the p AOs 412 and 413. A second π-bond 420 results from sideways overlap of the p AOs 414 and 415 and is indicated by curves connecting the lobes of the p AOs 414 and 415. The π-bonds 418 and 420 each share a pair of electrons and inhibit molecular rotation about the σ-bonds 407 and 409, respectively. When molecule 100 is in the lowest energy co-planar conformation, as shown in FIG. 2A, the adjacent π-orbitals 418 and 420 are in the same phase, which is represented in FIG. 4A by the lobes of the p AOs 413-415 having the same shading above and below segments 104 and 106. As a result, the π-bond electrons are delocalized over a large portion of molecule 100. This conformation is considered to place the molecule in an "ON" state. The π-bond electrons can tunnel between adjacent π-orbitals 418 and 420, as indicated by dashed lines 422 and 424. However, delocalization of electrons across rotator 106 and segment 104 is sensitive to the relative orientation of rotator 106 and segment 104. Electron tunneling between adjacent π-orbitals 418 and 420 can be destroyed when the rotator 106 is rotated away from 0 degrees, as shown in FIG. 2B. In particular, when the rotator 106 is rotated so that the rotation angle θ is between about 10 degrees and about 170 degrees, the probability of an electron tunneling between adjacent pi orbits 418 and 420 is very small. The π-bond electrons are localized, or electronic delocalization is reduced. The conformation is considered to place the molecule 100 in an "OFF" state. For example, as shown in FIG. 4B, the rotator 106 is rotated about the sigma bond 110 and into alignment with the direction of the external electric field 208. The lobes of π-orbitals 418 and 420 are no longer in phase or aligned. As a result, the probability of electrons tunneling between the π-orbitals 418 and 420 is negligible.

Figure 5:
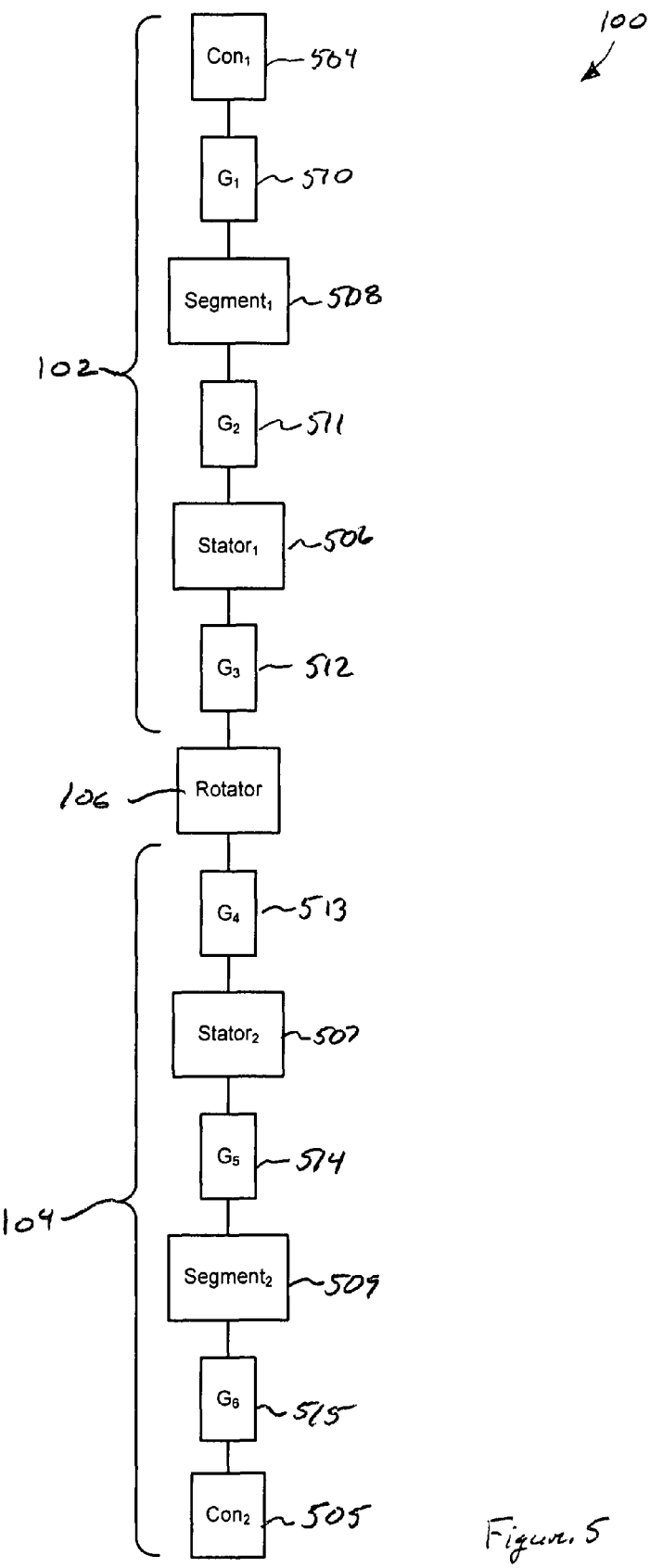
FIG. 5 shows a block-diagram of molecular sub-segments of the molecule shown in FIG. 1 that represents one embodiment of the present invention.

In various embodiments of the present invention, segments 102 and 104, described above with reference to FIG. 1, can be composed of many different kinds molecules, each molecule exhibiting a different property according to how molecule 100 is intended to be used and on the length of molecule 100 needed for particular applications. FIG. 5 shows a block-diagram representation of molecular sub-segments of segments 102 and 104 that represents one of many embodiments of the present invention. In FIG. 5, segments 102 and 104 are expanded in order to describe the kinds of molecules that can be used to configure molecule 100. In particular, segments 102 and 104 are each composed of six molecular sub-segments 504-515, described below, that are connected by single bonds.

Rotator 106 is a molecular moiety that can rotate under the influence of an applied external electric field, as described above with reference to FIGS. 2-4. Rotator 106 includes a hydrocarbon system with a dipole moment or tautomerizable bonds. Suitable hydrocarbon systems include: an aromatic ring, a saturated hydrocarbon, an unsaturated hydrocarbon, and a substituted hydrocarbon. Rotator 106 may include an electron acceptor group that can draw electron density away from the hydrocarbon system through electron delocalization. Examples of acceptor groups include: H; carboxylic acid and its derivatives; sulfuric acid and its derivatives; phosphoric acid and its derivatives; nitro; nitrile; heteroatoms, including N, O, S, P, F, Cl and Br; functional groups with at least one of the heteroatoms, including OH, SH, NH, PH; saturated or unsaturated hydrocarbons; and substituted hydrocarbons. Rotator 106 may also include an electron donator group that can provide electron density to the hydrocarbon system through electron delocalization. Examples of electron donator groups include: amine; OH; SH; ether; saturated hydrocarbon; unsaturated hydrocarbons; substituted hydrocarbons; and functional groups with at least one heteroatom, including B, Si, I, N, O, S, P. The electron donor group is differentiated from the acceptor group by being less electronegative than the acceptor group and, therefore, establishing a dipole moment across the rotator 106.

Molecule 100 may optionally include connector sub-segments "con1" 504 and "con2" 505, located at opposite ends of molecule 100. Connectors 504 and 505 can be included in order to bind the ends of molecule 100 to two different molecules, to a molecule and a substrate, or to two different substrates. The substrates can be electrodes, molecular wires, or non-electrodes, depending on the application. The composition of connectors 504 and 505 can be identical or different depending on the composition of the electrodes or substrates used to bind molecule 100. Suitable connectors 504 and 505 include: H for hydrogen bonding; multivalent heteroatoms, including C, N, O, S, or P; functional groups containing heteroatoms, including NH, OH, SH, and PH; saturated hydrocarbon; unsaturated hydrocarbons; and substituted hydrocarbons.

Molecule 100 may optionally include nonpolar stationary molecule units called "stators," attached to rotator 106 via σ-bonds and are identified as "stator$_1$" 506 and "stator$_2$" 507. Stators 506 and 507 provide support and room for the rotator 106 to rotate unobstructed through the rotation angle θ. Stators 506 and 507 can be identical or different conjugated systems that contribute to conjugation of molecule 100. Suitable stators 506 and 507 include: saturated hydrocarbons, unsaturated hydrocarbons, substituted hydrocarbons, and may include spacing groups that provide a three-dimensional scaffolding for supporting molecule 100 and providing the space needed for rotator 106 to rotate unobstructed through the rotation angle θ.

Molecule 100 may also include light emitting molecules "molecule$_1$" 508 and "molecule$_2$" 509 allowing the molecule 100 to used as a dye or a sensor. Suitable molecules 508 and 509 include: hydrocarbon and substituted hydrocarbon; polyaromatic hydrocarbons; and heterocyclic molecules. Molecules 508 and 509 may additionally include fluorescent or phosphorescent molecules that, when stimulated by an external light source, emit fluorescent or phosphorescent light, respectively. Using the molecule 100 as a dye or a sensor is described below with reference to FIG. 10.

Molecule 100 may optionally includes bridging groups represented by $G_1$ 510, $G_2$ 511, $G_3$ 512, $G_4$ 513, $G_5$ 514, and $G_6$ 515. Bridging groups $G_3$ 510 and $G_4$ 511 connect rotator 106 to stators 506 and 507, respectively; bridging groups $G_1$ 510 and $G_2$ 511 connect molecule 508 to connector 504 and to stator 506, respectively; and bridging groups $G_5$ 514 and $G_6$ 515 connect molecule 508 to stator 507 and to connector 505, respectively. Suitable bridging groups include: acetylene, ethylene, amide, imide, and azo. Bridging group $G_3$ 512 and $G_4$ 513 connecting stators 506 and 507 to rotator 106 may alternatively include a single atom bridge, such as an ether bridge with O, or represent σ-bonds.

Figure 6:
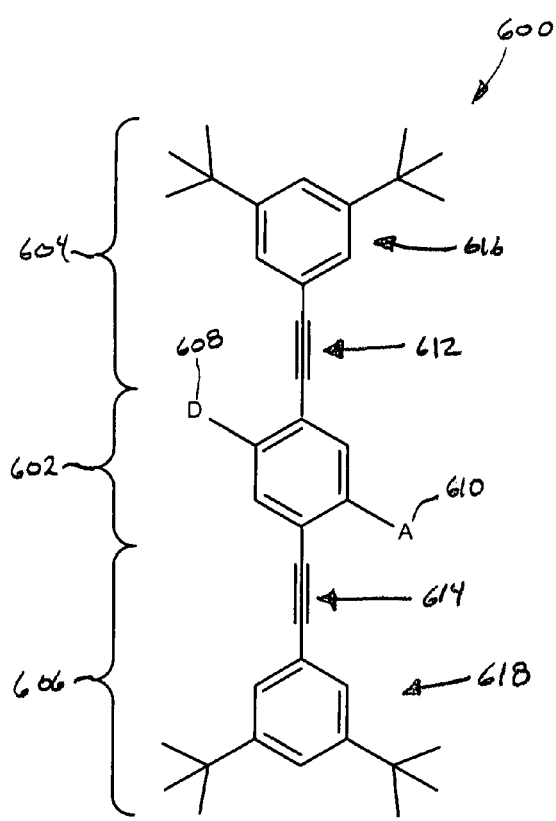
FIG. 6 shows the molecular structures of a first subclass of molecules that represent embodiments of the present invention.

FIG. 6 shows the molecular structures of a first subclass of molecules that represent embodiments of the present invention. A molecule 600 includes a rotator 602 and two identical segments 604 and 606. Rotator 602 is composed of benzene, a donor group D 608, and an acceptor group A 610 bonded to the benzene opposite donor group 608. Donor group 608 and acceptor group 610 can be any combination of donor and acceptor groups described above with reference to FIG. 5. Segments 604 and 606 include bridging groups 612 and 614 and two 3,5-di-tert-butylphenyl groups 616 and 618. Molecule 600 is an example of a molecule according to embodiments of the present invention that can be used in a molecular switch, a dye, or a sensor.

Figure 7:
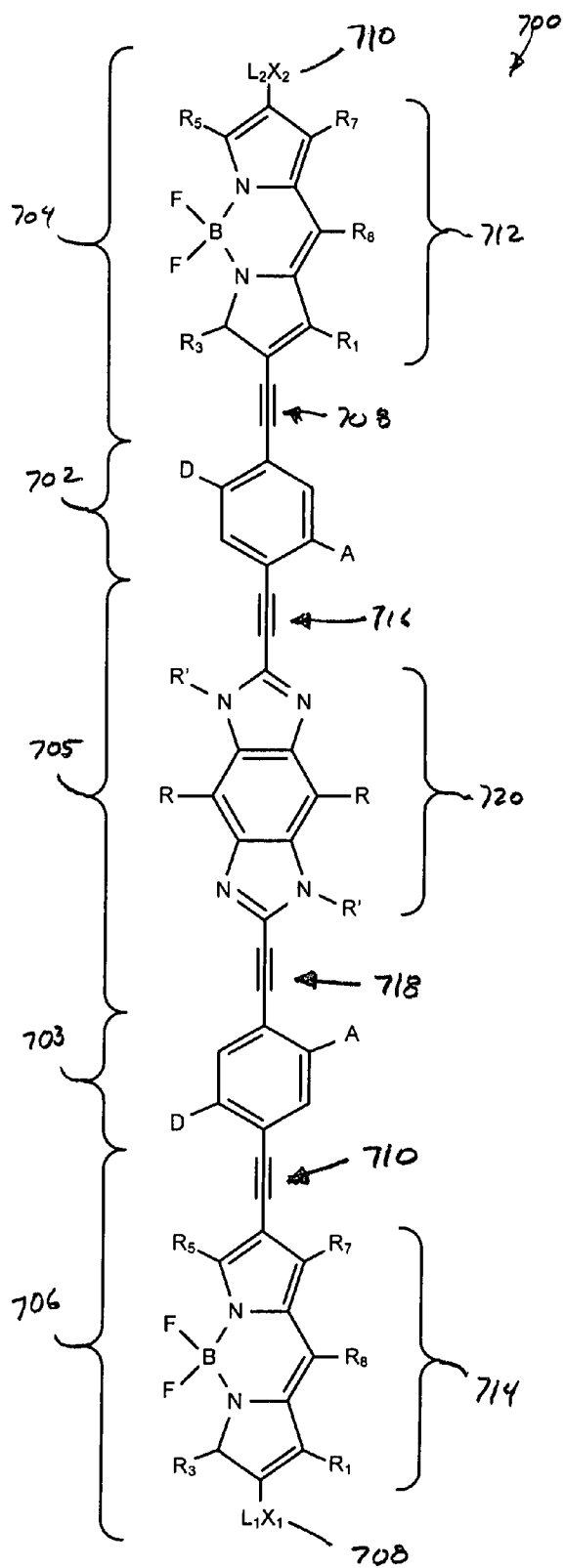
FIG. 7 shows the molecular structures of a second subclass of molecules that represent embodiments of the present invention.

FIG. 7 shows the molecular structures of a second subclass of molecules that represent embodiments of the present invention. A molecule 700 includes two rotators 702 and 703, and three segments 704-706. Rotators 702 and 703 are identical to the rotator 602, shown in FIG. 6. Donor group D and acceptor group A can be any combination of donor and acceptor groups described above with reference to FIG. 5, and the donor and acceptor groups associated with rotator 702 can be different from the donor and acceptor groups associated with rotator 703. Molecule 700 includes a first connector $L_1X_1$ 708 and a second connector $L_2X_2$ 710. Connectors 708 and 710 are optional, but when employed, connectors 708 and 710 can be identical or different molecules. Suitable connectors 708 and 710 include: 3-mercaptophenyl, 3-mercaptomethylphenyl, 3-(2-(4-mercaptophenyl)ethynyl)phenyl, 3-(2-(3-mercaptomethylphenyl)ethynyl)phenyl, 3-(2-(3-hydroselenophenyl)ethynyl)phenyl), 3-hydrotellurophenyl, 3-hydrotelluromethylphenyl, 3-(2-(4-hydrotellurophenyl)ethynyl)phenyl, and 3-(2-(3-hydrotellurophenyl)ethynyl)phenyl. Segments 704 and 706 include bridging groups 708 and 710, respectively, and molecules 712 and 713. Molecules 712 and 713 include atoms and molecules represented by $R_1$, $R_3$, $R_5$, $R_7$, and $R_8$, which may or may not be identical and can be a combination of atoms and molecules including: hydrogen atoms; saturated hydrocarbons; unsaturated hydrocarbons; substituted hydrocarbons; aryl groups; substituted aryl groups; and a functional group containing N, O, S, P, or As. Segment 705 includes two bridging groups 716 and 718 and a stator 720. Stator 720 includes spacer molecules represented by R and R' that allow rotators 702 and 703 to rotate and maintain separation from neighboring molecules.

Figure 8:
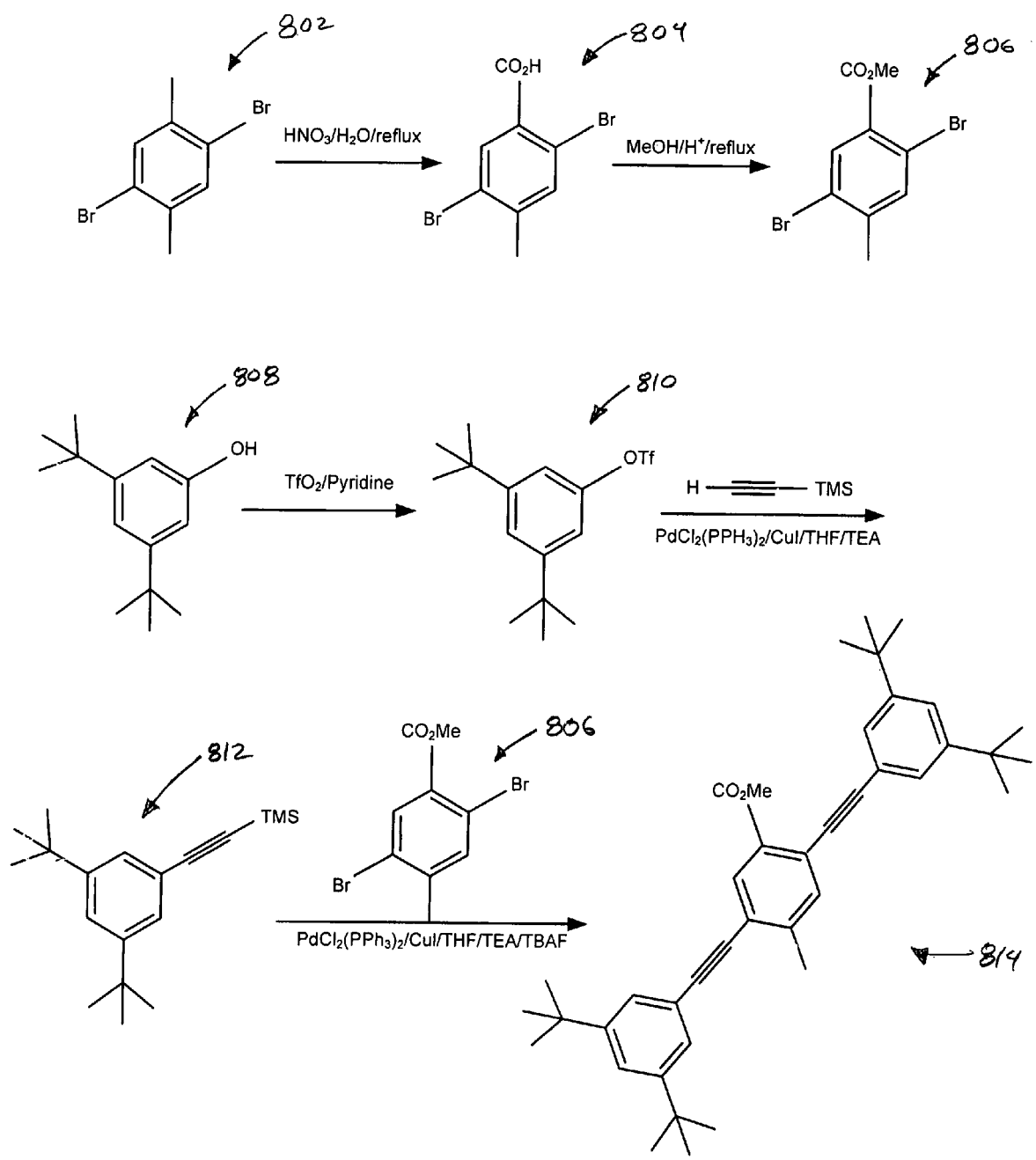
FIG. 8 shows a method for synthesizing a molecule belonging to the subclass shown in FIG. 6 according to one embodiment of the present invention.

Molecules of the present invention can be synthesized using well-known organic synthesis methods. FIG. 8 shows a method for synthesizing a molecule belonging to the subclass shown in FIG. 6 according to one embodiment of the present invention. A detailed description of the organic synthesis is described below in an experimental subsection called "Synthesis of 1,4-bis[3',5'-di-tert-butylphenylethynyl]-5-methyl-2-methoxycarbonylbenzene." The organic synthesis includes adding nitric acid and water to a solution of 2,5-dibromo-p-xylene 802, which is refluxed to obtain in solution 2,5-dibromo-4-methylbenzoic acid 804. Methanol and concentrated sulfuric acid are added to the solution of 2,5-dibromo-4-methylbenzoic acid 804, which is refluxed to obtain a solution of methyl 2,5-dibromo-4-methylbenzoate 806. In a separate part of the synthesis, trifluoromethanesulfonic anhydride and pyridine are added to a solution of 3,5-di-tert-butylphenol 808 and the solution is warmed to room temperature to obtain 3,5-di-tert-butylphenyl triflate 810. A solution of 3,5-di-tert-butylphenyl triflate 810, $PdCl_2$, $(PPH_3)_2$, CuI, tetrabutylammonium iodide, and trimethylsilylacetylene are stirred to obtain 1-[3',5'-di-tert-butylphenyl-2-trimethylsilylacetylene 812. Combining 1-[3',5'-di-tert-butylphenyl-2-trimethylsilylacetylene 812, methyl 2,5-dibromo-4-methylbenzoate 806, $PdCl_2$, $(PPH_3)_2$, CuI, triethylamine, tetrahydrofuran, and tetrabutylammonium fluoride and stirring at room temperature yields the desired molecule 1,4-bis[3',5'-di-tert-butylphenylethynyl]-5-methyl-2-methoxycarbonylbenzene 814.

In order to use the molecules of the present invention in a dye, a sensor, or molecular switch, the molecules are switched between the ON and OFF states, described above with reference to FIG. 4. This may be accomplish in certain embodiments of the present invention, by positioning the molecules between a pair of electrodes so that an electric field with an appropriate magnitude and orientation, produced between the two electrodes, causes the rotator of the molecules to be rotated away from a co-planar conformation. The orientation of a molecule located between two electrodes can vary depending on the type of molecule selected and how the molecule is used.

Figure 9A:
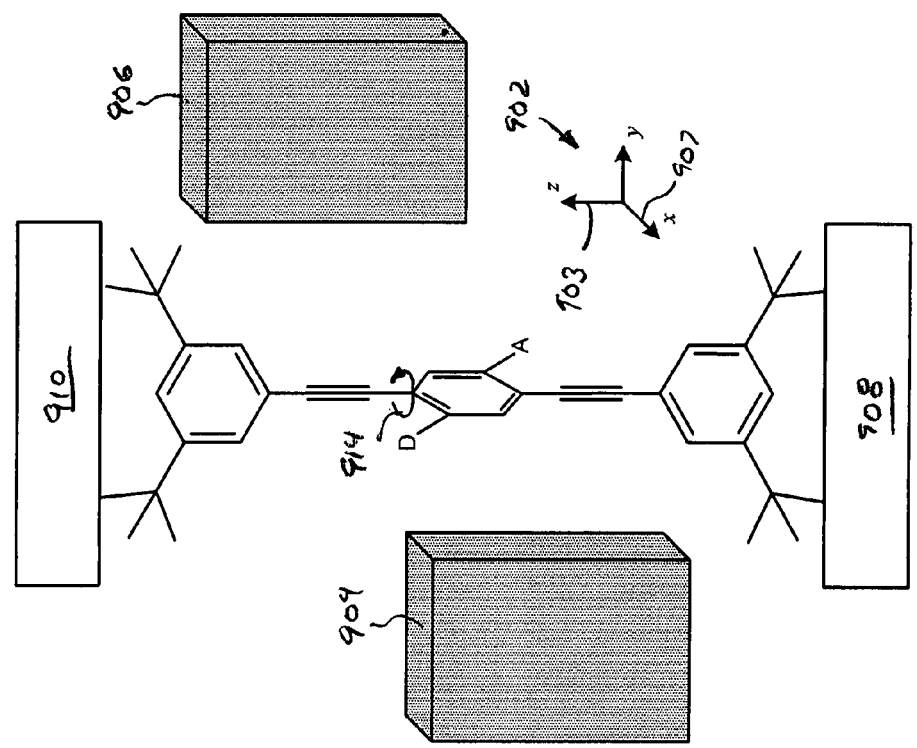
FIGS. 9A-9B show two ways in which a molecule can be positioned between two electrodes, each of which represents an embodiment of the present invention.
Figure 9A:
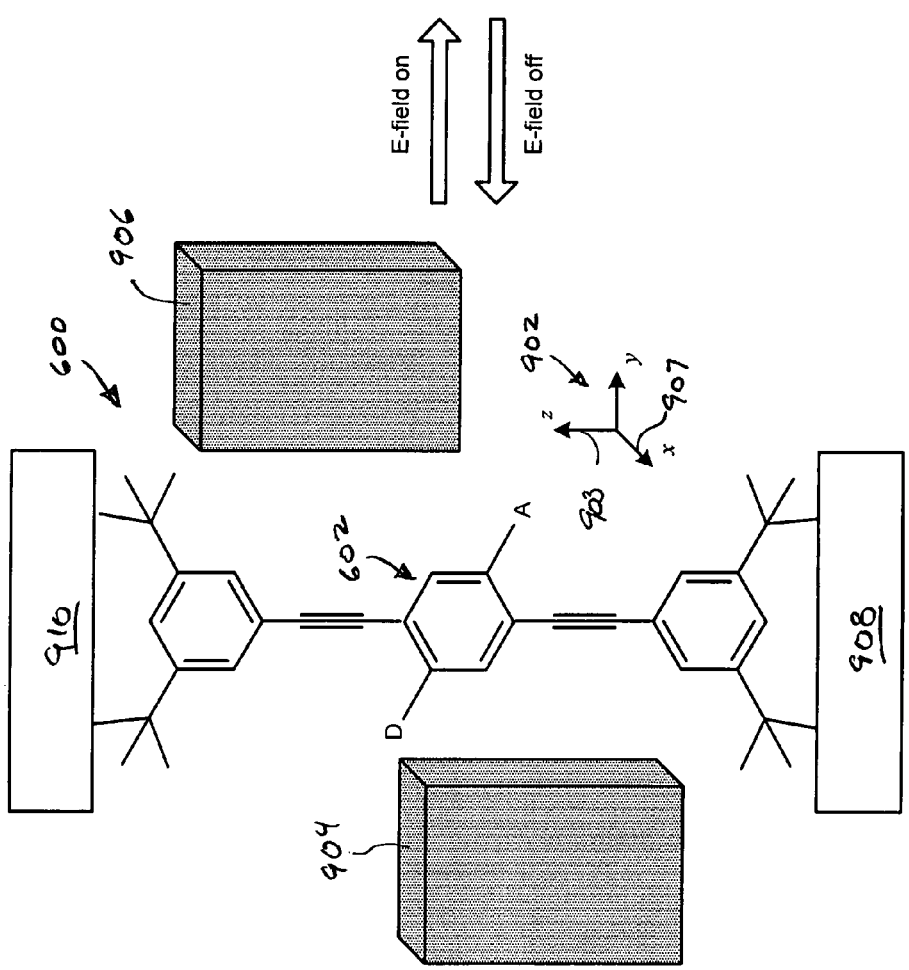
Figure 9B:
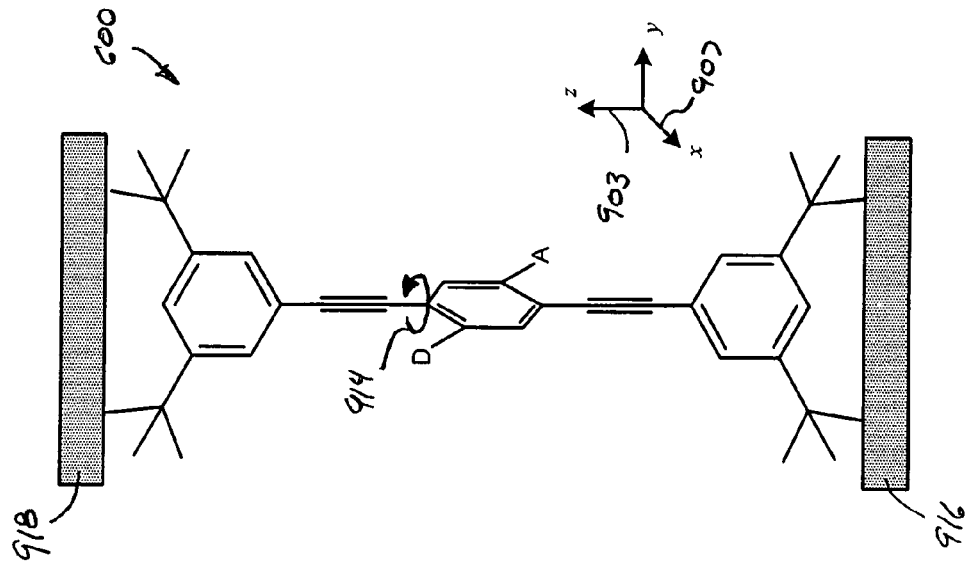
Figure 9B:
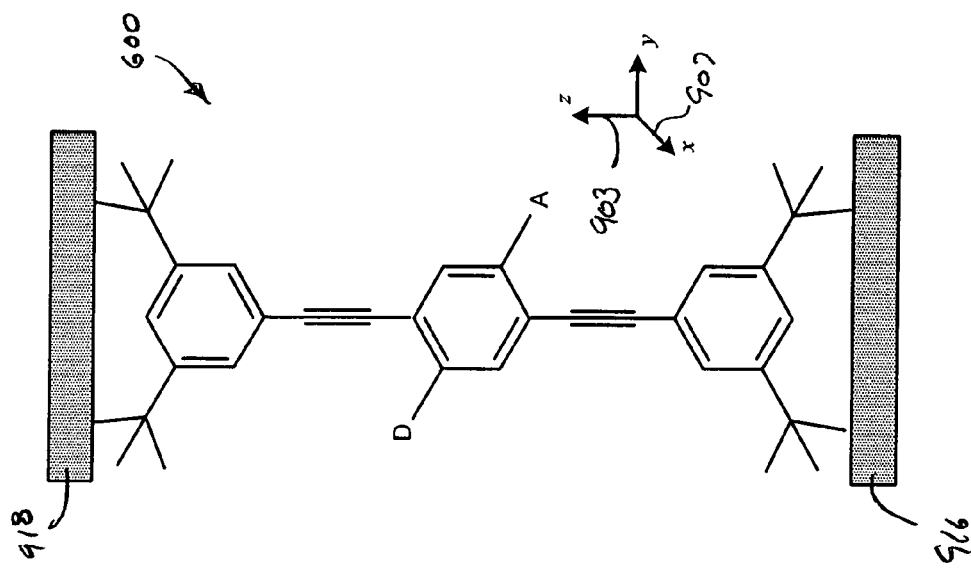

FIGS. 9A-9B show two ways in which a molecule can be positioned between two electrodes, each of which represents an embodiment of the present invention. A Cartesian coordinate system 902 is included in the FIGS. 9A-9B in order to describe the relative orientation of molecule 600, shown in FIG. 6, with respect to two electrodes 904 and 906. As shown in FIGS. 9A-9B, the central axis of molecule 600 is parallel to the z-coordinate axis 903. FIG. 9A shows molecule 600 bonded to a first support structure 908 and a second support structure 910 located along the central axis of molecule 600. Electrodes 904 and 906 are positioned on opposite sides of molecule 600 and located along an axis that is substantially parallel to the x-coordinate axis 907. As shown in FIG. 9A, initially all three of the aromatic rings of molecule 600 lie in the yz-plane. However, when an appropriate voltage is applied to electrodes 904 and 906, an electric field is created between the electrodes 904 and 906. This electric field causes rotator 602 to rotate 914 about the central axis of molecule 600 and out of the yz-plane. FIG. 9B shows molecule 600 attached to a first electrode 916 and a second electrode 918 located along the central axis of molecule 600. As shown in FIG. 9B, initially all three of the aromatic rings of molecule 600 lie in the yz-plane. When an appropriate voltage is applied to electrodes 916 and 918, an electric field is created between electrodes 916 and 918, which causes rotator 602 to rotate 914 about the central axis of molecule 600 and out of the yz-plane.

In dye and sensor embodiments of the present invention, segments 102 and 104 of molecule 100 can be synthesized to include fluorophores or phosphorescent units. When molecule 100 is in the ON state, either or both segments 102 and 104 may absorb light of one wavelength and emit light of a second wavelength. When molecule 100 is in the OFF state, segments 102 and 104 may emit light of a third wavelength or not at all. Molecule 814, shown in FIG. 8, is an example of a molecule that emits fluorescent blue light when molecule 814 is in the co-planar conformation. However, when the rotator of molecule 814 is rotated away from the co-planar conformation, molecule 814 does not fluoresce.

Figure 10A:
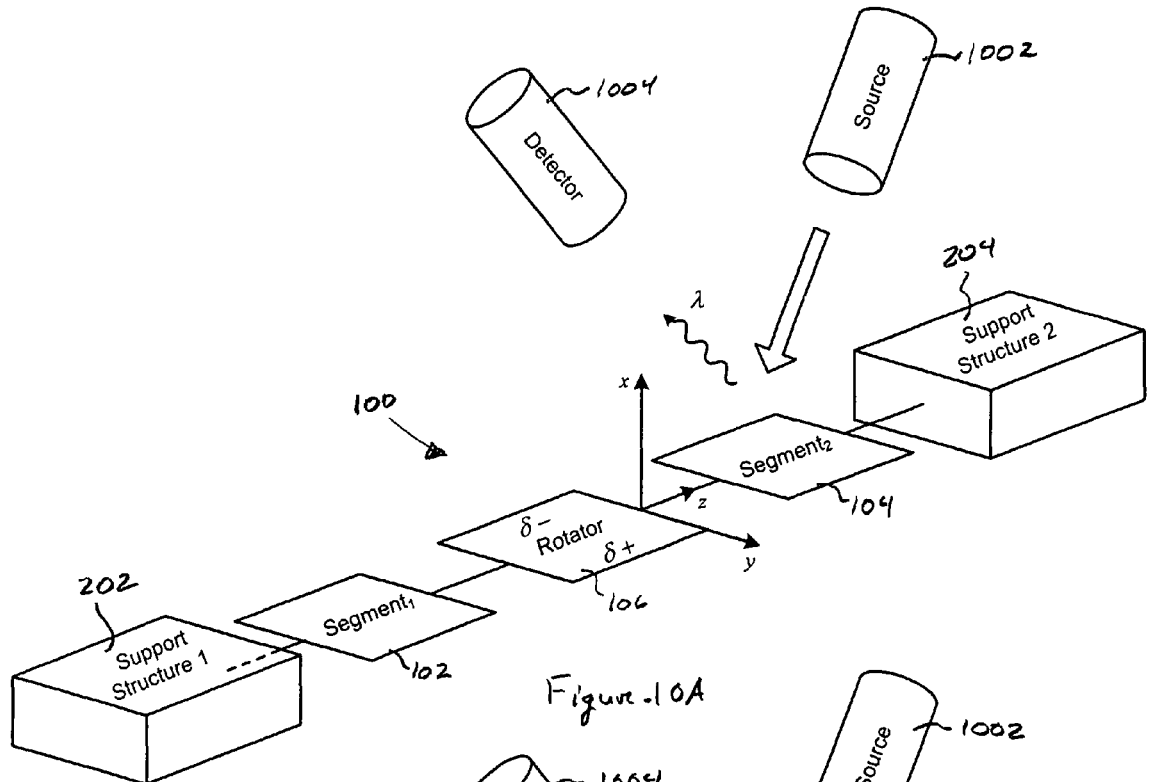
FIGS. 10A-10B illustrate use of the molecule shown in FIG. 1 as a tunable dye and sensor according to one embodiment of the present invention.
Figure 10B:
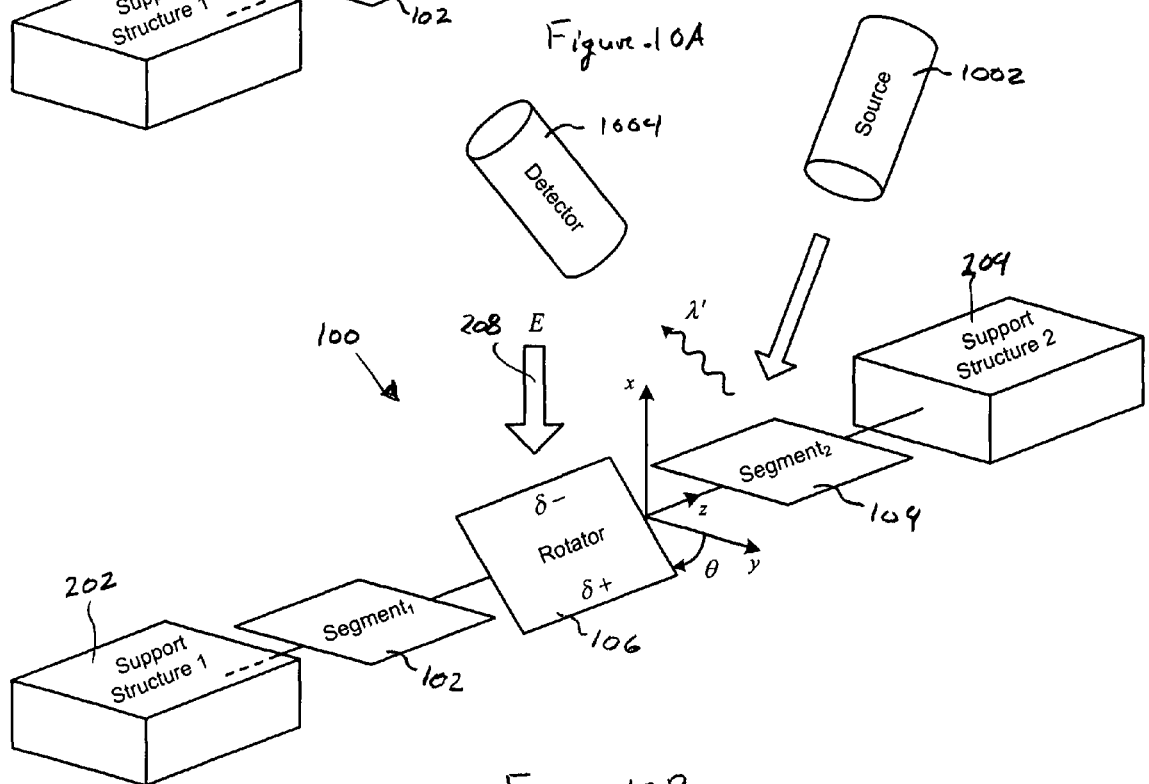

FIGS. 10A-10B illustrate use of the molecule shown in FIG. 1 as a tunable dye and sensor according to one embodiment of the present invention. In FIG. 10A, molecule 100 is initially in the ON state, and light emitted from a source 1002 causes an emission of light form segment 104 with a wavelength $\lambda$, which is detected by a detector 1004. Depending on the composition of segment 104, source 1002 can be a laser that emits light in the ultraviolet, visible, or infrared regions of the electromagnetic spectrum. By contrast, as shown in FIG. 10B, external electric field 208 causes rotator 106 to rotate away from the co-planar conformation shown in FIG. 10A. As a result, molecule 100 is in the OFF state, and light emitted by source 1002 causes an emission of light form segment 104 with a different wavelength $\lambda'$, which is detected by a detector 1004. In certain embodiments of the present invention, the wavelength of the light emitted from the molecule 100 can be tuned by controlling the amount rotator 106 is rotated. In other embodiments of the present invention, the fluorescence or phosphorescence of molecule 100 may be turned off when the rotator 106 is slightly rotated away from the co-planar conformation. Molecule 100 can be used as a sensor by configuring segments 102 and 104 to bind certain analytes. Molecule 100 operates as a sensor by emitting light of a particular wavelength when an analyte is bound to either of the segments 102 and 104.

In other embodiments of the present invention, molecule 100 can be used as a molecular switch in molecular electronics. FIGS. 11A-11B illustrate use of the molecule shown in FIG. 1 as a molecular switch according to one embodiment of the present invention. A switch 1100 includes molecule 100 bonded to two wires 1102 and 1104. Segment 102 is bonded to wire 1102, and segment 104 is bonded to wire 1104. These bonds can be hydrogen, covalent, or ionic bonds. Wires 1102 and 1104 are connected to a voltage source 1108 and can be composed of Au, Cu, Pt, Al, or any other suitable conductor material. FIG. 11A shows switch 1100 in the ON state. When molecule 100 is in the ON state, the conjugated $\pi$-bonds allow an electronic current 1110 to flow through molecule 100. FIG. 11B shows switch 1100 in the OFF state. When external electric field 208 is applied to rotator 106, the electronic delocalization is reduces and electronic current flowing between the conjugated $\pi$-bonds of the rotator 106 and segments 102 and 104.

Synthesis of 1,4-bis[3',5'-di-tert-butylphenylethynyl]-5-methyl-2-methoxycarbonylbenzene To a mixed solution of nitric acid (45 ml, 70-71%) and water (55 ml) was added portionwise 2,5-dibromo-p-xylene 802 (13.2 g, 50 mmol). The resulting mixture was heated to reflux and continued to reflux for 6 days. The mixture was cooled to room temperature and the white solid was collected by filtration. The solid was placed into a mixture of ethyl acetate (100 ml) and water (100 ml), to which was added sodium carbonate portion wise (ca 10-12 g) over a 2 hour period until all the solid dissolved. The organic layer was separated and the aqueous layer was made strongly acidic by the addition of concentrated HCl to pH 2-3. A white solid was collected by filtration and dried in vacuum to give 2,5-dibromo-4-methylbenzoic acid: 9.6 g (65%).

To a solution of 2,5-dibromo-4-methylbenzoic acid 5.88 g, 20 mmol) in 50 mL of methanol was added 0.2 mL of concentrated sulfuric acid. The resulting solution was refluxed for 24 hours. Evaporation of the solvent gave a residue, which was redissolved into 100 mL of ethyl acetate. The organic layer was washed with saturated sodium biocarbonate solution, water and brine. The resulting organic layer was dried over sodium sulfate. Filtration off sodium sulfate and evaporation of the solvent gave methyl 2,5-dibromo-4-methylbenzoate as a white solid: 6.20 g (100%).

To a solution of 3,5-di-tert-butylphenol (10.32 g, 50 mmol) in pyridine (40 mL) was added trifluoromethanesulfonic anhydride (15.60 g, 9.3 mL, 55.31 mmol) at 0° C. under nitrogen. After the addition, the reaction was warmed to room temperature and continuously stirred at room temperature overnight. Then water was added and the product was extracted with hexanes (3×50 mL). The combined organic layer was washed with 10% HCl aqueous solution and brine. The resulting organic layer was dried over sodium sulfate. Filtration of sodium sulfate and evaporation of the solvent gave 3,5-di-tert-butylphenyl triflate as a white solid: 17.0 g (100%) as a pale yellow oil.

A solution of 3,5-di-tert-butylphenyl triflate (6.76 g, 20 mmol), PdCl$_2$ (PPH$_3$)$_2$ (350 mg, 0.5 mmol), CuI (190 mg, 1.0 mmol), tetrabutylammonium iodide (7.37 g, 20 mmol) and trimethylsilylacetylene (2.95 g, 4.24 mmol, 30 mmol) in 20 mL of triethylamine and 30 mL of dimethyldoramide was stirred at room temperature overnight. Then, the mixture was partitioned between hexanes and water (50 ml/50 ml). The aqueous later was extracted with ethyl acetate (50 mL). The combined organic layer was washed with water and brine and dried over sodium sulfate. Filtration off sodium sulfate and evaporation of the solvent followed by purification by flash chromatography gave 1-[3',5'-di-tert-butylphenyl-2-trimethylsilylacetylene as a pale yellow solid: 5.20 g (91%).

To a solution of 1-[3',5'-di-tert-butylphenyl-2-trimethylsilylacetylene (572 mg, 2.0 mmol), methyl 2,5-dibromo-4-methylbenzoate 806 (308 mg, 1.0 mmol), PdCl$_2$ (PPH$_3$)$_2$ (100 mg, 0.1 mmol), CuI (20 mg, 0.1 mmol), in 10 mL of triethylamine and 10 mL of tetrahydrofuran was added to 2.5 mL of tetrabutylammonium fluoride. The resulted solution was stirred at room temperature for overnight. Then, the mixture was partitioned between ethylacetate and water (50 ml/50 ml). The aqueous later was extracted with ethyl acetate (50 mL). The combined organic layer was washed with water, brine abd dried over sodium sulfate. Filtration off sodium sulfate and evaporation of the solvent followed by purification by flash chromatography gave 1,4-bis[3',5'-di-tert-butylphenylethynyl]-5-methyl-2-methoxycarbonylbenzene as a pale yellow solid: 390 mg (68%).

Although the present invention has been described in terms of particular embodiments, it is not intended that the invention be limited to these embodiments. Modifications within the spirit of the invention will be apparent to those skilled in the art. In other embodiments of the present invention, those skilled in the art would recognize that the rotator 106 can be composed of a molecule without acceptor and donator regions but polarizes under the influence of an external electric field. In other embodiments of the present invention, the class of molecules includes molecules with two or more rotators.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:
1. A molecule having a structure:

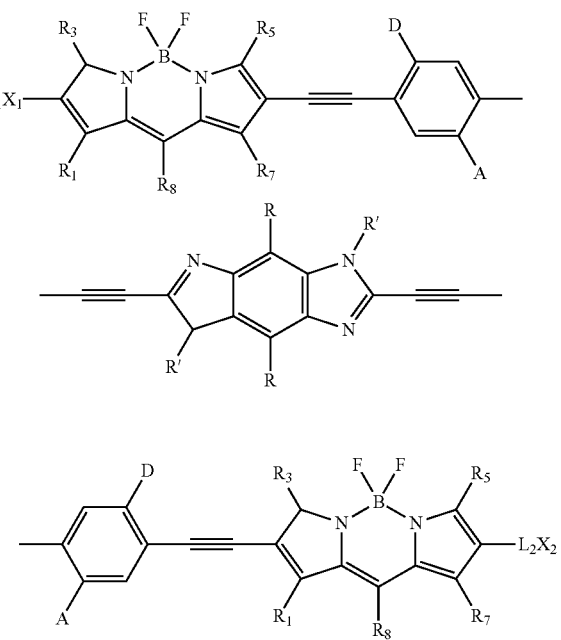

where $L_1X_1$ and $L_2X_2$ are connectors, A represents an electron acceptor, D represents an electron donor, R and R' represent spacer molecules, and $R_1$, $R_3$, $R_5$, $R_7$, and $R_8$ represent hydrogen atoms and hydrocarbons.

2. The molecule of claim 1 wherein $L_1X_1$ and $L_2X_2$ can be independently selected from: 3-mercaptophenyl,
   3-mercaptomethylphenyl,
   3-(2-(4-mercaptophenyl)ethynyl)phenyl,
   3-(2-(3-mercaptomethylphenyl)ethynyl)phenyl,
   3-(2-(3-hydroselenophenyl)ethynyl)phenyl),
   3-hydrotellurophenyl,
   3-hydrotelluromethylphenyl,
   3-(2-(4-hydrotellurophenyl)ethynyl)phenyl, and
   3-(2-(3-hydrotellurophenyl)ethynyl)phenyl.

3. The molecule of claim 1 wherein the electron donor D can be one of: an amine, OH, SH, an ether, a saturated hydrocarbon, an unsaturated hydrocarbon, a substituted hydrocarbon, and a functional group.

4. The molecule of claim 3 wherein the functional group further comprises one of: B, Si, I, N, O, S, and P.

5. The molecule of claim 1 wherein $R_1$, $R_3$, $R_5$, $R_7$, and $R_8$ can be independently selected from: H; a saturated hydrocarbon; an unsaturated hydrocarbon; a substituted hydrocarbon; an aryl; a substituted aryl; and a functional group containing N, O, S, P, or As.

6. A molecular switch comprising:
a first wire and a second wire; and
the molecule of claim 1 having a first end bonded to the first wire and a second end bonded to the second wire.

7. A sensor comprising:
a first support structure and a second support structure;
the molecule of claim 1 having a first end bonded to the first support structure and a second end bonded to the second support structure;
an electromagnetic radiation source to illuminate the molecule; and
a detector to detect light emitted from the molecule.

* * * * *

UNITED STATES PATENT AND TRADEMARK OFFICE
CERTIFICATE OF CORRECTION

PATENT NO. : 8,044,212 B2
APPLICATION NO. : 11/799147
DATED : October 25, 2011
INVENTOR(S) : Zhang-Lin Zhou et al.

Page 1 of 2

It is certified that error appears in the above-identified patent and that said Letters Patent is hereby corrected as shown below:

In column 10, line 30-35 (approx.), in Claim 1, delete

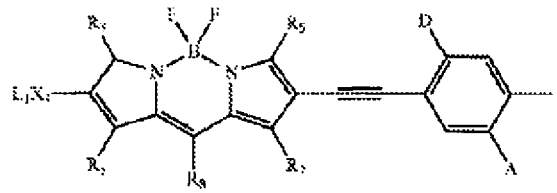

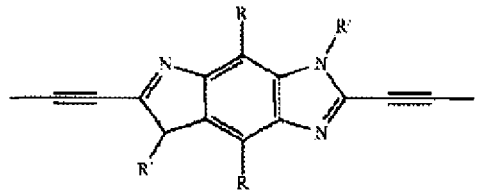

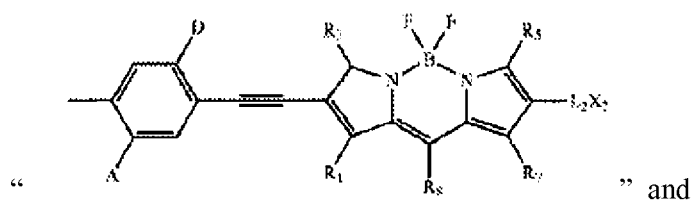

" and insert

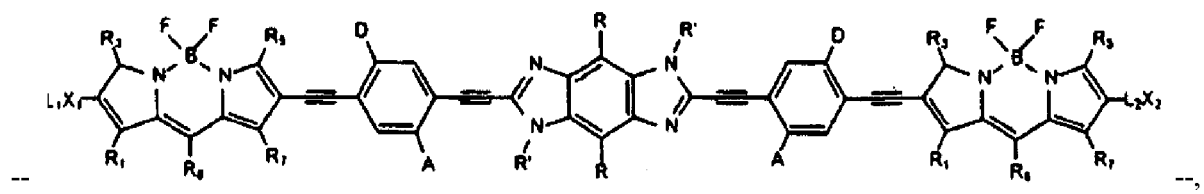

-- --, therefor.

Signed and Sealed this
Seventeenth Day of July, 2012

David J. Kappos
*Director of the United States Patent and Trademark Office*

CERTIFICATE OF CORRECTION (continued)
U.S. Pat. No. 8,044,212 B2

In column 10, line 57 (approx.), in Claim 2,
delete "3-(2-(3-hydroselenophenyl)ethynyl)phenyl)," and
insert -- 3-(2-(3-hydroselenophenyl)ethynyl)phenyl, --, therefor.